United States Patent [19]

Ownby

[11] 3,981,822

[45] Sept. 21, 1976

[54] NOVEL COMBINATIONS OF ULTRAVIOLET STABILIZERS AND THEIR USE IN ORGANIC COMPOSITIONS

[75] Inventor: James C. Ownby, Kingsport, Tenn.

[73] Assignee: Eastman Kodak Company, Rochester, N.Y.

[22] Filed: Sept. 19, 1975

[21] Appl. No.: 615,032

[52] U.S. Cl............................ 252/403; 252/392; 260/45.8 SN; 260/45.8 NZ; 260/45.8 N; 260/45.8 RW; 260/45.8 NT; 260/45.9 R
[51] Int. Cl.² .................. C09K 15/30; C09K 15/28; C09K 15/16
[58] Field of Search........................... 252/403, 392; 260/45.8 SN, 45.8 NZ, 45.8 N, 45.8 RW, 45.8 NT, 45.9 R

[56] References Cited
UNITED STATES PATENTS

| | | | |
|---|---|---|---|
| 3,206,428 | 9/1965 | Stanley .............................. | 252/403 |
| 3,380,981 | 4/1968 | Dressler et al...................... | 252/403 |
| 3,425,804 | 2/1969 | Flinn et al.......................... | 252/403 |
| 3,493,510 | 2/1970 | Chao................................... | 252/403 |
| 3,720,616 | 3/1973 | Randell et al...................... | 252/403 |
| 3,723,428 | 3/1973 | Song................................... | 252/403 |

Primary Examiner—Benjamin R. Padgett
Assistant Examiner—Irwin Gluck
Attorney, Agent, or Firm—Clyde L. Tootle; Daniel B. Reece, III

[57] ABSTRACT

The invention relates to combinations of compounds which have been found to produce more effective ultraviolet stabilization. The invention also relates to ultraviolet degradable organic compositions containing a stabilizing amount of these ultraviolet stabilizer combinations to prevent such degradation. These stabilizer combinations are effective in the presence of other additives commonly employed in polymeric compositions including, for example, pigments, colorants, fillers, reinforcing agents and the like. These ultraviolet stabilizer combinations may also be incorporated into the organic compositions in the polymer melt or dissolved in the polymer dope, coated on the exterior of the molded article, film or extruded fiber.

14 Claims, No Drawings

NOVEL COMBINATIONS OF ULTRAVIOLET STABILIZERS AND THEIR USE IN ORGANIC COMPOSITIONS

This invention relates to combinations of ultraviolet stabilizers and their use in organic compositions. More particularly, the invention relates to combinations of ultraviolet compositions and the stabilization of ultraviolet degradable organic compositions against deterioration resulting from the exposure to such radiations with such compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effort, there have been discovered many additives and stabilizers which improve the stability of polymeric compositions.

Moreover, various additives and stabilizers exhibit the power to absorb ultraviolet radiation within the band of 2900 to 4000 A. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

It is still another object of the present invention to provide compositions containing a combination of ultraviolet stabilizers which are resistant to ultraviolet degradation.

It is a still further object of this invention to provide processes for improving the resistance of organic materials to deterioration and degradation by actinic radiation and especially ultraviolet radiation.

It is a still further object of this invention to provide combinations of stabilizers which compositions and processes improve the resistance of organic materials to deterioration and degradation by actinic radiations, including short wave-length visible radiations.

Further objects and advantages of the invention will be apparent to those skilled in the art from the accompanying disclosure and claims.

In accordance with the present invention, combinations of ultraviolet stabilizers are provided which are useful as ultraviolet stabilizers or ultraviolet screening agents. These combinations of stabilizers contain at least one heterocyclic compound having the following structures:

A-I or A-B-C wherein A is a group having the structure

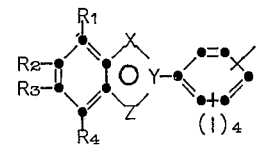

wherein

X and Y are a carbon atom, a carbon atom containing an R group or a nitrogen atom;

Z is an oxygen atom, a sulfur atom, a nitrogen atom, or a nitrogen atom containing a hydrogen atom or a substituted or unsubstituted lower alkyl group containing 1 to 12 carbon atoms or an aryl or substituted aryl group having 6 to 18 carbon atoms;

R, $R_1$, $R_2$, $R_3$ and $R_4$ are hydrogen, lower alkyl, substituted lower alkyl, cycloalkyl, substituted cycloalkyl, aryl, chloro, bromo, substituted aryl, lower alkylaryl, aryl-substituted-aryl, alkoxy, carboalkoxy, substituted amino, cyano, and the substituents $R_1$ and $R_2$, $R_2$ and $R_3$ and $R_3$ and $R_4$, combined with the carbon atoms to which they are attached, are joined alkylene groups completing a carbocyclic ring which ring can be substituted with any of the substituents listed above for $R_1$, $R_2$, $R_3$ and $R_4$.

I is the same as $R_1$, $R_2$, $R_3$ and $R_4$ is present on all positions of the benzenoid ring, except the carbon atom attached to the Y substituent and the carbon atom attached to the carboxyl group connecting the heterocyclic aromatic A group with the aromatic B group. The carboxyl connecting group is attached to the benzene ring in either the meta or para position from the carbon atom connected to Y or is connected directly to Y. The I substituents can all be one of the substituents listed above or different listed substituents.

Suitable A groups having the structure

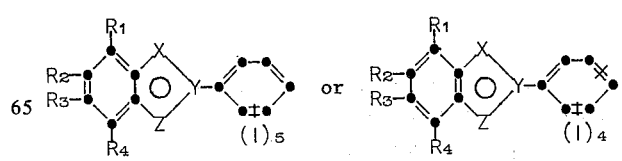

are, for example, substituted and unsubstituted benzoxazoles, benzotriazoles, benzothiazoles, benzimidazoles and indoles.

Examples of such suitable benzoxazole moieties are those having the formula

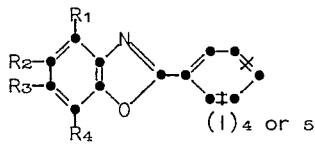

such as 4-(5,6-dimethyl-2-benzoxazolyl)phenyl, 4-(2-benzoxazolyl)-2-chlorophenyl, and 3-(5-chloro-2-benzoxazolyl)phenyl.

Examples of suitable benzotriazole moieties are those having the formula

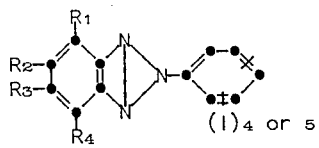

such as substituted and unsubstituted benzotriazoles such as 4-(5-chloro-2H-benzotriazol-2-yl)phenyl, 4-(2H-benzotriazol-2-yl)phenyl, 4-(5-methoxy-2H-benzotriazol-2-yl)phenyl, 2,5-dimethyl-4-(2H-benzotriazol-2-yl)phenyl, 2,5-dimethyl4-(5-chloro-2H-benzotriazol-2-yl)phenyl, 2-methyl-4-(2H-benzotriazol-2-yl)phenyl, 2-methyl-4-(5-chloro-2H-benzotriazol2-yl)phenyl, 2-chloro-4-(2H-benzotriazol-2-yl)phenyl, 2,5-dichloro-4-(2H-benzotriazol-2-yl)phenyl, 2-chloro-4-(5-chloro-2H-benzotriazol-2-yl)phenyl, 2,6-dichloro-4-(5-chloro-2H-benzotriazol-2-yl)phenyl, 2,6-dimethyl-4-(5-methoxy-2H-benzotriazol-2-yl)phenyl, 2,6-dimethyl-4-(5-methoxy-2H-benzotriazol-2-yl)phenyl, 2,6-dichloro-4-(5-methoxy-2H-benzotriazol-2-yl)phenyl, 2-chloro-4-(5-methoxy-2H-benzotriazol-2-yl)phenyl, 2-methyl-4-(5-methoxy-2H-benzotriazol-2-yl)phenyl 2-phenyl-4-(2H-benzotriazol-2-yl)phenyl, 4-methyl-2-(5-chloro-2H-benzotriazol-2-yl)phenyl, 4-methyl-2-(5-methoxy-2H-benzotriazol-2-yl)phenyl, 4-(4,6-dichloro-2H-benzotriazol-2-yl)phenyl, 4-(4,6-dimethyl-2H-benzotriazol-2-yl)phenyl, 4-methyl-2-(2H-benzotriazol-2-yl)phenyl, and the like.

Examples of suitable benzothiazole moieties are those having the formula

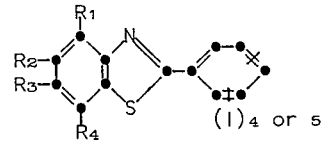

such as 4-(5,6-dimethyl-2-benzothiazolyl)phenyl, 4-(2benzothiazolyl)-2-chlorophenyl, and 3-(5-chloro-2-benzothiazolyl)phenyl, 2-(2-benzothiazolyl)phenyl, 4-(2-benzothiazolyl)phenyl, and the like.

Examples of suitable benzimidazole moieties are those having the formula

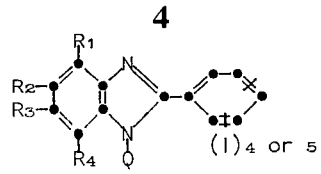

wherein Q is hydrogen or a substituted or unsubstituted lower alkyl group containing 1 to 12 carbon atoms, such as 4-(5,6-dimethyl-2-benzimidazolyl)phenyl, 4-(2-benzimidazolyl)-2-chlorophenyl, 3-(5-chloro-2-benzimidazolyl)phenyl, 4-(1-methyl-2-benzimidazolyl)phenyl, 4-(1-ethyl-5-chloro-2-benzimidazolyl)phenyl, 3-(1-ethyl-2-benzimidazolyl)phenyl, 2-(1-methyl-2-benzimidazolyl)phenyl, and 2-(1-ethyl-5-chloro-2-benzimidazolyl)phenyl.

Examples of suitable indole moieties are those having the formula

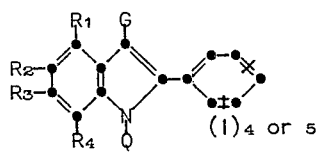

wherein G is the same as $R_1$ and Q is hydrogen or a substituted or unsubstituted lower alkyl containing 1 to 12 carbon atoms, such as 3-(1-ethyl-3-cyano-2-indolyl)phenyl, 3-(5-chloro-2-indolyl)phenyl, 3-(1-methyl-2-indolyl)phenyl, 3-(3-methyl-2-indolyl)phenyl, 3-(3-chloro-2-indolyl)phenyl, 3-(5-acetamido-2-indolyl)phenyl, 3-(2-indolyl)phenyl, 4-(1-ethyl-2-indolyl)phenyl, 4-(3-cyano-2-indolyl)phenyl, 4-(5-methoxy-2-indolyl)phenyl, 4-(1-methyl-2-indolyl)phenyl, 4-(3-methyl-5-phenyl-2-indolyl)phenyl, 4-(3,5-dichloro-2-indolyl)phenyl, 4-(2-indolyl)phenyl, 4-chloro-2-indolylphenyl, 2-(1-methyl-2-indolyl)phenyl and 2-(1-ethyl-3-cyano-2-indolyl)phenyl.

B is a linking group connecting A and C and can be alkylene, arylene, carbonyl, carbonyloxy, oxycarbonylalkyleneoxy, oxycarbonyl, alkyleneoxycarbonyloxy, oxyalkylenecarbonyl, oxycarbonyloxy, alkyleneoxy, oxyalkylene, alkyleneoxyalkyleneoxy, thio, thioalkyleneoxy, sulfinyldioxy, oxy(alkoxy)phosphinooxy, alkyloxyphosphinylidene, aryloxyphosphinylidene, oxy(alkyl)phosphinyloxy, aminocarbonyl, N-alkylaminocarbonyl, N-arylaminocarbonyl, aminocarbonylalkyleneoxy, N-alkylaminocarbonylalkyleneoxy, N-arylaminocarbonylalkyleneoxy, aminocarbonylamino, N-alkylaminocarbonylamino, N,N-dialkylaminocarbonyl, N-arylaminocarbonyl, N-alkylaminocarbonyl, N,N-diarylaminocarbonyl, amino, N-alkylamino, N-arylamino, N-alkylaminoalkyleneoxy, N-arylaminoalkyleneoxy, oxyalkyleneoxy, oxyaryleneoxy, alkyleneaminoalkylene, aryleneaminoarylene, aryleneaminoalkylene and alkyleneaminoarylene; and wherein C is a hydroxybenzophenone group having the formula

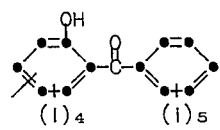

where I is the same substituent as listed above and is present in all positions of the benzenoid rings except the carbon atom attached to the B group connecting the A and C moieties, said B connecting group is attached to the benzenoid ring in the ortho, meta or para position from the keto group of the benzophenone, and said I substituents can all the one of the substituents listed above or different listed substituents.

In combination with the heterocyclic compound, the stabilizing composition contains an aryl benzoate or a benzophenone. Such benzoate or benzophenones have the formula:

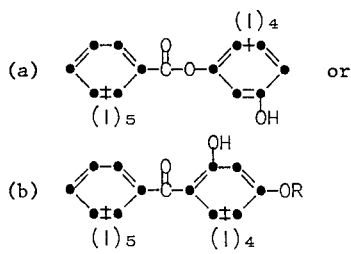

the aryl ester is capable by the "photo-Fries" rearrangement of forming a phenol group in that position formerly joined through an oxygen atom to the carbonyl linking group, as for example:

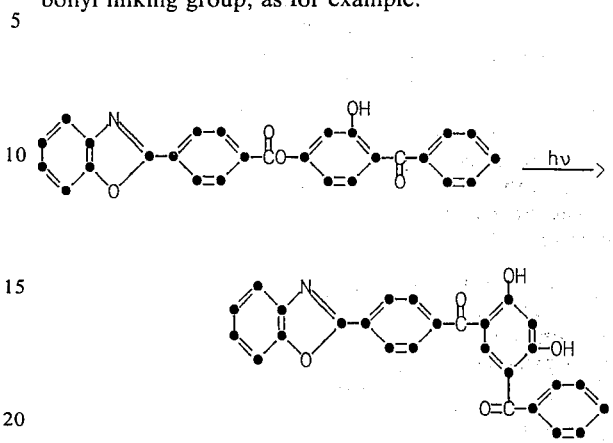

wherein R is hydrogen or an alkyl group of 1 to 20 carbon atoms (e.g., methyl, 2-ethylhexyl, decyl, docecyl, octadecyl, and the like).

Certain of the heterocyclic ester compositions can be prepared by reacting an acid chloride with a phenol. For example, one group of such organic compounds useful as ultraviolet stabilizers is, for example, compositions having the following structures

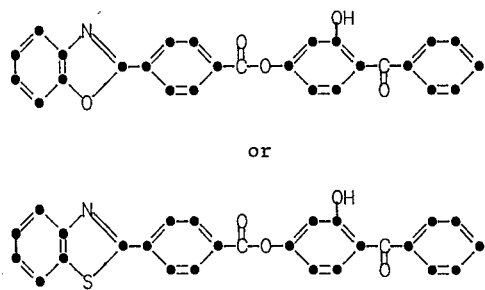

One method for preparing these compounds is by the following procedure:

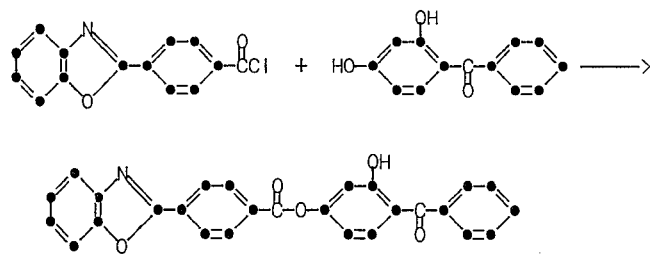

When the B group is a carboxyl group, it is desirable that at least one carbon atom adjacent to the carbon atom attached to the carboxy oxygen contain a hydrogen substituent so that on exposure to ultraviolet light, This example hereinabove shows the B linking group as a carboxyl group. Other Blinking groups can be provided as known in the art, as for example:

1. an oxycarbonylalkyleneoxy by esterification of an acid or acid chloride with an alcohol or phenol in alkaline medium;
2. an oxycarbonyloxy by the reaction of phosgene with alcohol or phenol in alkaline medium;
3. an alkyleneoxy by the reaction of halide with alkali salt of alcohol or phenol;
4. an alkyleneoxyalkyleneoxy by the reaction of halide with alkali salt of alcohol or phenol;
5. a sulfinyldioxy by the reaction of thionyl chloride with alcohol or phenol in alkaline solution;
6. a thio by the reaction of a sodium sulfide with a halide;
7. an oxy(alkoxy)phosphinooxy by the reaction of a dichlorophosphite with phenol in the presence of a base;
8. an N-alkyl or N-arylaminocarbonyl by the reaction of an acid chloride with an amine;
9. an N-alkyl or N-arylaminocarbonylalkoxy by the reaction of an acid chloride with an amine;
10. an N-alkyl or N-arylaminocarbonylamino by the reaction of phosgene with an amine;
11. an N-alkyl or N-arylaminoalkylene by the reaction of an alkyl halide with an amide;
12. an N-alkyl or N-arylaminoalkyleneoxy by the reaction of an oxyalkyl halide with an amine.

The acid chlorides were prepared by reaction of the corresponding acid [See Zh. Obshch. Khim., 38, 100 1-5 (1968); Chem. Abstr. 69 96568 (1968)] with freshly distilled thionyl chloride [See J. Chem. Soc. 101, 2476 (1912)]. The dihydroxy benzophenones were obtained from commercial sources, or were prepared by standard methods.

The stabilizing combination of at least one heterocyclic compound and at least one diaryl benzoate or benzophenone provides a synergistic stabilizing effect. For example, the heterocyclic compound such as a benzotriazole or a benzoxazole are effective stabilizers for polyesters. However, to be useful in commercial polyester applications the heterocyclic compound when used alone must be used in a concentration of about 0.5 weight percent. The addition of an aryl benzoate or benzophenone provides a stabilizing combination which provides effective stabilization containing only 0.2% by weight or less of the heterocyclic compound.

The stabilizing combination can be added to organic compositions which are susceptible to ultraviolet degradation. Such compositions include, for example, polymeric compositions such as polyester fiber and molding compositions, such as polyethylene terephthalate, poly(tetramethylene terephthalate) and the like; polyolefins such as, for example, high, medium and low density polyethylene, polypropylene, polybutene and the like; polyamides such as nylon 6, nylon 66, N-methoxymethyl polyhexamethylene adipamide and the like; polycarbonates; polyvinyl chlorides and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals, polyformaldehydes; and polyurethanes. Such compositions also include natural and synthetic rubbers, such as polybutadiene, and unsaturated organic compositions such as oils and the like, as well as compositions containing such organic compositions.

about 0.1 to about 2.5%, by weight of heterocyclic compound. For example, an amount of 0.2%, by weight of heterocyclic compound and 0.8% benzoate effectively stabilizes cellulose acetate butyrate and polyester such as poly(tetramethylene terephthalate) plastic compositions.

The ultraviolet stabilized organic compositions of the present invention may also contain other additives, pigments, colorants, fillers, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel stabilizer combinations may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1 p-4-dodecyloxy-2-hydroxybenzophenone) 4-(2-benzoxazolyl) benzoate can be prepared by the following procedure:

To a solution of 0.8 g. (0.02 mole) of sodium hydroxide in 50 ml. of water was added 4.22 g. (0.02 mole) of 4-dodecyloxy-2,4'-dihydroxybenzophenone. The mixture was stirred for 10 minutes and 150 ml. of chloroform 5.16 g. (0.02 mole) of 4-(2-benzoxazolyl)benzoyl chloride was added dropwise. The mixture was stirred at reflux for 15 hours after the addition was completed. The reaction mixture was cooled to 30°C. and a solid separated out between the layers. This was filtered and air-dried and amounted to 8.0 g. (93%) of I (mp 295°–300°).

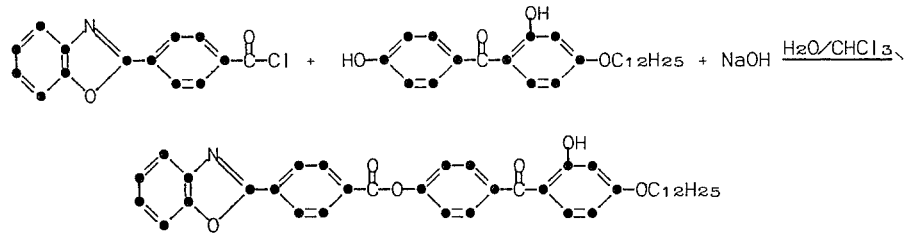

The stabilizing combination, as an effective ultraviolet stabilizer or screening agent, is generally used in an amount of from 0.01 to 5%, by weight, based on the weight of the organic material to which they are added. While a detectable amount of ultraviolet screening and stabilization may be obtained with amounts less then 0.01%, this amount of stabilization or screening would be of little practical utility in a commercial application. Moreoever, while amounts greater than 5%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from Other heterocyclic stabilizer compounds can be prepared by substitution of other benzophenones.

Also, other heterocyclic stabilizer compounds can be prepared by substituting other benzoxazolylbenzoyl chlorides, such as 4-(5,6-dimethyl-2-benzoxazolyl)-benzoyl chloride, 4-(2-benzoxazolyl)-2-chlorobenzoyl chloride, 3-(5-chloro-2-benzoxazolyl)benzoyl chloride, 4-(5,6-dichloro-2-benzoxazolyl benzoyl chloride, 4-(5,6-diethyl-2-benzoxazolyl)benzoyl chloride, 4-(5-cyano-2-benzoxazolyl)benzoyl chloride, 4-(5-methoxy-6-methyl-2-benzoxazolyl)benzoyl chloride, for 4-(2-benzoxazolyl)-benzoyl chloride.

These compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

Weathering data results shown in Table I illustrate the stabilization obtained with the combination of stabilizers of this invention.

Table 1

Weathering of Poly(tetramethylene terephthalate) Polyester

| Additive | Flatwise Impact Strength After Mercury Lamp Exposure For Hours Indicated | | | |
|---|---|---|---|---|
| | Initial | 500 hr. | 1000 hr. | 1500 hr. |
| None | 20 | 1 | | |
| NS-2 (0.2%)* | 18 | 19 | 2 | 1 |
| NS-2 (0.5%) | 19 | 20 | 9 | 2 |
| RMB (0.5%)** | 18 | 1 | | |
| NS-2 (0.2%) + RMB (0.8%) | 18 | 19 | 18 | 14 |
| DOBP (0.5%)*** | 19 | 20 | 2 | 2 |
| NS-2 (0.2%) + DOBP (0.8%) | 18 | 19 | 15 | 10 |

*NS-2 is 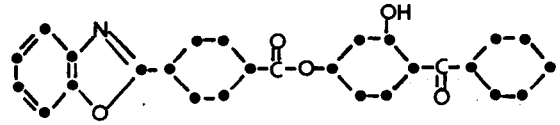

**RMB is 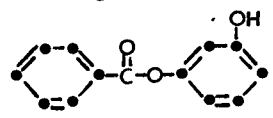

***DOBP is 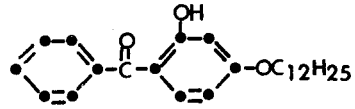

EXAMPLE 2

Samples prepared as in Example 1 and irradiated in Uvatest Model 110 weathering device using 366-nm and 310-nm fluorescent tubes (data in Table 2).

Table 2

Effectiveness of Ultraviolet Stabilizers in Poly(Tetramethylene Terephthalate) Polyester

| Stabilizers (wt. %) (+0.5% Weston 618) | Uvatest (FWIS — Flatwise Impact Strength) | | | | |
|---|---|---|---|---|---|
| | Initial | 250 hr. | 500 hr. | 750 hr. | 1000 hr. |
| None | 17 | 1 | — | — | — |
| RMB (0.5%) | 18 | 6 | 1 | 1 | 1 |
| Tinuvin P (0.5%) | 18 | 14 | 11 | 9 | 3 |
| Tinuvin P (0.4%) + RMB (0.8%) | 19 | 20 | 20 | 6 | 12 |
| BTI (0.2%) | 18 | 19 | 13 | 5 | 2 |
| BTI (0.2%) + RMB (0.8%) | 18 | 20 | 20 | 19 | 17 |
| BTB (0.2%) | 18 | 20 | 4 | 2 | 2 |
| BTB (0.2%) + RMB (0.8%) | 18 | 20 | 20 | 19 | 15 |
| PBOX (0.2%) | 18 | 20 | 11 | 5 | 2 |
| PBOX (0.2%) + RMB (0.8%) | 18 | 20 | 20 | 19 | 10 |
| NS-2 (0.2%) | 18 | 19 | 5 | 2 | 2 |
| NS-2 (0.2%) + RMB (0.8%) | 18 | 20 | 18 | 19 | 11 |

BTI = Bis[P-(2H-benzotriazol-2-yl)phenyl] isophthalate.
BTB = p-(2H-Benzotriazol-2-yl) phenyl benzoate.
PBOX = m-Phenylene bis(p-2-benzoxazolylbenzoate).
Weston 618 is a commercially available phosphite stabilizer sold by Weston Chemical.

EXAMPLE 3

Samples irradiated in Atlax XWR Weather-Ometer using carbonarc light source. Data in Table 3.

Table 3

Effectiveness of Ultraviolet Stabilizers in Poly(Tetramethylene Terephthalate) Polyester*

| Stabilizers (wt. %) (+0.5% Weston 618) | Atlas XWR Weather-Ometer Exposure (Flatwise Impact Strength) | | | | | |
|---|---|---|---|---|---|---|
| | Initial | 250 hr. | 500 hr. | 750 hr. | 1000 hr. | 1500 hr. |
| None | 17 | 1 | 1 | — | — | — |
| RMB (0.5%) | 18 | 5 | 1 | 1 | 1 | 1 |
| RMB (1.0%) | 18 | 5 | 1 | 1 | 1 | 1 |
| RMB (2.0%) | 18 | 11 | 11 | 11 | 11 | 1 |

Table 3-continued

Effectiveness of Ultraviolet Stabilizers in Poly(Tetramethylene Terephthalate) Polyester*

| Stabilizers (wt. %) (+0.5% Weston 618) | Atlas XWR Weather-Ometer Exposure (Flatwise Impact Strength) | | | | | |
|---|---|---|---|---|---|---|
| | Initial | 250 hr. | 500 hr. | 750 hr. | 1000 hr. | 1500 hr. |
| Tinuvin P (0.5%) | 18 | 20 | 20 | 20 | 12 | 7 |
| Tinuvin P (0.25%) + RMB (0.4%) | 18 | 19 | 2 | 3 | 2 | 2 |
| BTI (0.2%) | 18 | 17 | 5 | 2 | 3 | 2 |
| BTI (0.2%) + RMB (0.8%) | 18 | 20 | 18 | 21 | 15 | 17 |
| BTB (0.2%) | 18 | 14 | 2 | 2 | 2 | 2 |
| BTB (0.2%) + RMB (0.8%) | 18 | 20 | 20 | 21 | 9 | 11 |
| PBOX (0.2%) | 18 | 18 | 12 | 2 | 5 | 7 |
| PBOX (0.2%) + RMB (0.8%) | 18 | 20 | 20 | 19 | 14 | 16 |
| NS-2 (0.2%) | 18 | 18 | 7 | 2 | 2 | 2 |
| NS-2 (0.2%) + RMB (0.8%) | 18 | 20 | 20 | 21 | 3 | 9 |

*BTI = Bis[p-(2H-benzotriazol-2-yl)phenyl] isophthalate.
BTB = p-(2H-Benzotriazol-2-yl) phenyl benzoate.
PBOX = m-Phenylene bis(p-2-benzoxazolylbenzoate).

The invention has been described in detail with particular reference to preferred embodiments thereof, but it will be understood that variations and modifications can be effected within the spirit and scope of the invention.

I claim:
1. An organic composition susceptible to ultraviolet light degradation stabilized against such degradation with a stabilizing amount of a mixture of:
   1. at least one heterocyclic compound having the formula:

A-I or A-B-C wherein A is a group having the structure

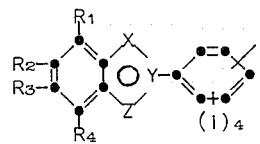

wherein
   X and Y are a carbon atom, a carbon atom containing an R group or a nitrogen atom;
   Z is an oxygen atom, a sulfur atom, a nitrogen atom, or a nitrogen atom containing a hydrogen atom or an alkyl group having 1 to 12 carbon atoms or an aryl or substituted aryl group having 6 to 18 carbon atoms;
   R, $R_1$, $R_2$, $R_3$ and $R_4$ are hydrogen, chloro, bromo, lower alkyl, substituted lower alkyl, cycloalkyl, substituted cycloalkyl, aryl, substituted aryl, lower alkylaryl, aryl-substituted-aryl, alkoxy, substituted amino, cyano, carboalkoxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$;
   I is the same as $R_1$, $R_2$, $R_3$ and $R_4$ and is present on all positions of the benzenoid ring, except the carbon atom attached to the Y substituent and the carbon atom attached to the B group connecting the heterocyclic aromatic A group with the aromatic C group, said B connecting group is attached to the benzenoid ring in the ortho, meta or para positions from the carbon atom connected to the Y substituent, said I substituents can all be the same substituent listed above or different listed substituents;
   B is a linking group connecting A and C and can be alkylene, arylene, carbonyl, carbonyloxy, oxycarbonylalkyleneoxy, oxycarbonyl, alkyleneoxycarbonyloxy, oxyalkylenecarbonyl, oxycarbonyloxy, alkyleneoxy, oxyalkylene, alkyleneoxyalkyleneoxy, thio, thioalkyleneoxy, sulfinyldioxy, oxy(alkoxy)-phosphinooxy, alkyloxyphosphinylidene, aryloxyphosphinylidene, oxy(alkyl)phosphinyloxy, aminocarbonyl, N-alkylaminocarbonyl, N-arylaminocarbonyl, aminocarbonylalkyleneoxy, N-alkylaminocarbonylalkyleneoxy, N-arylaminocarbonylalkyleneoxy, aminocarbonylamino, N-alkylaminocarbonylamino, N,N-dialkylaminocarbonyl, N-arylaminocarbonyl, N-alkylaminocarbonyl, N,N-diarylaminocarbonyl, amino, N-alkylamino, N-arylamino, N-alkylaminoalkyleneoxy, N-arylaminoalkyleneoxy, oxyalkyleneoxy, oxyaryleneoxy, alkyleneaminoalkylene, aryleneaminoarylene, aryleneaminoalkylene and alkyleneaminoarylene; and
   wherein C is a hydroxybenzophenone group having the formula

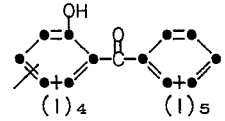

where I is the same substituent as listed above and is present in all positions of the benzenoid rings except the carbon atom attached to the B group connecting the A and C moieties, said B connecting group is attached to the benzenoid ring in the ortho, meta or para position from the keto group of the benzophenone, and said I substituents can all be one of the substituents listed above or different listed substituents, and
   2. at least one compound selected from the group consisting of:

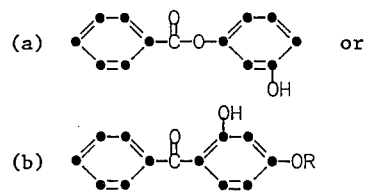

wherein R is hydrogen or an alkyl group of 1 to 20 carbon atoms.

2. An organic composition according to claim 1 wherein X is a carbon atom.

3. An organic composition according to claim 1 wherein X is a nitrogen atom.

4. An organic composition according to claim 2 wherein Y is a carbon atom.

5. An organic composition according to claim 3 wherein Y is a nitrogen atom.

6. An organic composition according to claim 3 wherein Y is a carbon atom.

7. An organic composition according to claim 6 wherein Z is a sulfur atom.

8. An organic composition according to claim 5 wherein Z is a nitrogen atom.

9. An organic composition according to claim 6 wherein Z is a nitrogen atom containing hydrogen or a substituted or unsubstituted lower alkyl group containing 1 to 12 carbon atoms.

10. An organic composition according to claim 6 wherein Z is an oxygen atom.

11. A organic composition according to claim 10 wherein A is a group having the structure:

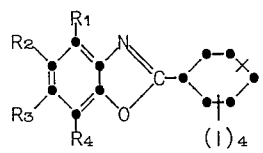

wherein
$R_1$, $R_2$, $R_3$ and $R_4$ are hydrogen, chloro, bromo, lower alkyl, substituted lower alkyl, cycloalkyl, substituted cycloalkyl, aryl, substituted aryl, lower alkylaryl, aryl-substituted-aryl, alkoxy, substituted amino, cyano, carboalkoxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$;

I is the same as $R_1$, $R_2$, $R_3$ and $R_4$ and is present on all positions of the benzenoid ring, except the carbon atom attached to the Y substituent and the carbon atom attached to the B group connecting the heterocyclic aromatic A group with the aromatic C group, said B connecting group is attached to the benzenoid ring in the ortho, meta or para positions from the carbon atom connected to the Y substituent, said I substituents can all be the same substituent listed above or different listed substituents;

B is a linking group connecting A and C and can be alkylene, arylene, carbonyl, carbonyloxy, oxycarbonylalkyleneoxy, oxycarbonyl, alkyleneoxycarbonyloxy, oxyalkylenecarbonyl, oxycarbonyloxy, alkyleneoxy, oxyalkylene, alkyleneoxyalkyleneoxy, thio, thioalkyleneoxy, sulfinyldioxy, oxy(alkoxy)phosphinooxy, alkyloxyphosphinylidene, aryloxyphosphinylidene, oxy(alkyl)phosphinyloxy, aminocarbonyl, N-alkylaminocarbonyl, N-arylaminocarbonyl, aminocarbonylalkyleneoxy, N-alkylaminocarbonylalkyleneoxy, N-arylaminocarbonylalkyleneoxy, aminocarbonylamino, N-alkylaminocarbonylamino, N,N-dialkylaminocarbonyl, N-arylaminocarbonyl, N-alkylaminocarbonyl, N,N-diarylaminocarbonyl, amino, N-alkylamino, N-arylamino, N-alkylaminoalkyleneoxy, N-arylaminoalkyleneoxy, oxyalkyleneoxy, oxyaryleneoxy, alkyleneaminoalkylene, aryleneaminoarylene, aryleneaminoalkylene and alkyleneaminoarylene; and wherein C is a hydroxybenzophenone group having the formula

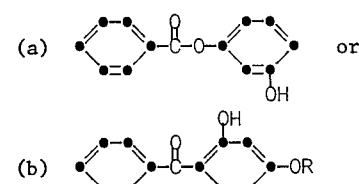

where I is the same substituent as listed above and is present in all positions of the benzoid rings except the carbon atom attached to the B group connecting the A and C moieties, said B connecting group is attached to the benzenoid ring in the ortho, meta or para position from the keto group of the benzophenone, and said I substituents can all be one of the substituents listed above or different listed substituents, and 2. at least one compound selected from the group consisting of:

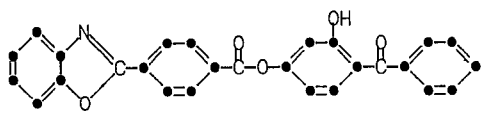

wherein R is hydrogen or an alkyl group of 1 to 20 carbon atoms.

12. An organic composition according to claim 11 wherein said heterocyclic compound has the formula:

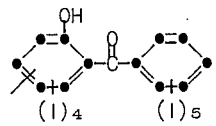

13. An organic composition according to claim 8 wherein said heterocyclic compound has the formula:

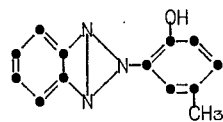

14. An organic composition according to claim 8 wherein said heterocyclic compound has the formula:

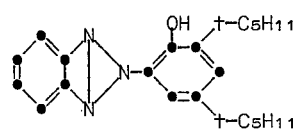

* * * * *